US011612848B1

(12) United States Patent
Bullard et al.

(10) Patent No.: US 11,612,848 B1
(45) Date of Patent: Mar. 28, 2023

(54) PEROXYCARBOXYLIC ACID SCRUBBER ASSEMBLY

(71) Applicant: Zee Company, Inc., Chattanooga, TN (US)

(72) Inventors: Robert C. Bullard, Signal Mountain, TN (US); Jonathon R. Bullard, Chattanooga, TN (US); James A. Faller, Chattanooga, TN (US); A. Rider Barnum, Hixson, TN (US); W. Joseph Guinn, Chattanooga, TN (US); Robert J. Matthews, Bridgeport, AL (US)

(73) Assignee: Zee Company I, LLC, Chattanooga, TN (US)

( * ) Notice: Subject to any disclaimer, the term of this patent is extended or adjusted under 35 U.S.C. 154(b) by 653 days.

(21) Appl. No.: 16/689,507

(22) Filed: Nov. 20, 2019

Related U.S. Application Data

(60) Provisional application No. 62/769,685, filed on Nov. 20, 2018.

(51) Int. Cl.
| | |
|---|---|
| *B01D 47/02* | (2006.01) |
| *B01D 53/04* | (2006.01) |
| *B01D 53/78* | (2006.01) |
| *A61L 2/18* | (2006.01) |
| *B01D 53/38* | (2006.01) |

(52) U.S. Cl.
CPC ............ *B01D 47/021* (2013.01); *A61L 2/186* (2013.01); *B01D 53/0446* (2013.01); *B01D 53/0454* (2013.01); *B01D 53/38* (2013.01); *B01D 53/78* (2013.01); *B01D 2257/90* (2013.01); *B01D 2258/0275* (2013.01)

(58) Field of Classification Search
CPC ............ B01D 53/0446; B01D 53/0454; B01D 53/14; B01D 53/34; B01D 53/38; B01D 53/78; B01D 2257/90; B01D 2258/0275; B01D 47/021; A61L 2/186; A61L 9/145; F23G 2209/14

See application file for complete search history.

(56) References Cited

U.S. PATENT DOCUMENTS

| | | | | |
|---|---|---|---|---|
| 2,720,386 | A * | 10/1955 | Bungas ................ | B01D 47/022 261/24 |
| 6,277,344 | B1 * | 8/2001 | Hei ........................ | B01D 53/38 423/220 |
| 8,128,742 | B1 * | 3/2012 | McGuffin ............... | B01D 47/04 96/353 |

* cited by examiner

*Primary Examiner* — Jonathan Miller
*Assistant Examiner* — Gabriel E Gitman
(74) *Attorney, Agent, or Firm* — DeWitt LLP

(57) ABSTRACT

A scrubbing assembly for treating malodorous air by chemical scrubbing one or more chemical components from an influent airflow, particularly one or more chemical components that have become airborne from chemical intervention solutions used during food processing, such as vapors from peroxycarboxylic acid solutions used during food processing. The peroxycarboxylic acid vapors are removed from air in a continuous manner within the scrubber assembly utilizing a neutralizing chemical solution to provide a treated effluent airflow that can be returned back to the point of use area from which the malodorous air was removed for treatment.

42 Claims, 3 Drawing Sheets

PEROXYCARBOXYLIC ACID SCRUBBER ASSEMBLY

CROSS-REFERENCE TO RELATED APPLICATIONS

The present application claims the benefit of U.S. Provisional Application No. 62/769,685 filed Nov. 20, 2018, which is hereby incorporated herein in its entirety by reference.

FIELD OF INVENTION

The present invention relates to a scrubber system, a scrubber assembly and methods of using a scrubbing assembly for air purification and/or deodorization of malodorous air by chemical scrubbing. In particular, the present invention relates to a peroxycarboxylic acid scrubber assembly that can be used to continuously treat air at a point of use by removing at least a portion of peroxycarboxylic acid vapors in the air resulting from processing of a food product. In particular, the peroxycarboxylic acid vapors in air can be a malodorous source in the air that can be removed from a point of use in a continuous manner within the scrubber assembly, particularly by continuously flowing the malodorous air having vaporous peroxycarboxylic acid, such as peroxyacetic acid, through a neutralizing chemical solution within the scrubbing assembly that treats the malodorous air before returning the treated air back to the same point of use area.

BACKGROUND OF THE INVENTION

The world population has grown to point where mass production of the foods that we consume is no longer a luxury but a requirement. Local farmers, providing food and food products directly to the marketplace, cannot meet the demands of modern society. The food supply chain now incorporates very large, complex farms and high speed and high volume processing plants to satisfy the need for mass processing and production of food. Maintaining a safe food supply chain relies on the dedication of those working in the supply chain, the processing plants and also on the third party oversight of various Federal agencies whose regulations support and mandate food safety.

With two major exceptions, the physical process of taking an animal from the farm to the consumer has changed very little over time. The introduction of refrigeration, and the implementation of various chemistries to help maintain sanitary conditions and to control microbiology, has given modern food processors an advantage not enjoyed by food producers of a century ago. Refrigeration and chemical intervention practices have become an integral part of food processing facility operations. These technologies have enabled the high speed, high volume output of the large processing facilities that could not have been possible in times past without significant concern for consumer safety. With large scale and continuous processing methods being employed by large processors of protein products, or any other product that is susceptible to microbiological contamination, the concern for the control of microbiology and the safety of the food supply chain is of paramount importance.

Another concern, as the demand for food products increases, is the impact on natural resources created by this demand. The ecological impact is directly affected by this growth and therefore new processes must be developed to reduce the impact any given process has on the environment.

The ecological impact that a food processing plant has on the environment is no longer a passing concern but a major part of operations and planning. Entire processes are built around the control and conservation of natural resources such as water. Older, outdated and less efficient processes are being replaced at significant cost with more efficient and less wasteful processes that maximizes the utility of available resources. No longer can a plant operate without concern for the conservation and sustainability of natural resources.

To insure that the food supply chain in modern society is maintained at the highest levels of safety for the consumer, the plant's employees, and the overall environment, there are federal agencies that monitor the processors operations so that a continually safe food supply is assured and the environmental impact and utilization of natural resources is as safe and efficient as possible.

Modern food processing methods are scrutinized by government agencies to ensure compliance with safe handling and processing guidelines designed to minimize issues of food safety in the supply chain Regulations and routine inspections of systems and processes by Federal agencies such as the USDA, EPA and OSHA, mandate a government-industry alliance that helps ensure that every effort is made to deliver the safest product possible to the consumer. The FDA also regulates food contact substances, such as chemical intervention solutions used during processing of food products to reduce microbial activity.

Very innovative approaches to the systems and methods used in processing facilities have been implemented to create profits for industry while maintaining low consumer cost of the final product. As new processes are developed, the federal agencies that have jurisdiction over any particular process are called upon to review the new approach and to ensure that the new innovation meets the current guidelines for safety. The higher the processors output, the higher the risk of microbiological contamination, and therefore the more innovative the processor must be to combat this ever present threat to the food chain safety. As new risks are found, federal guidelines become more stringent.

Large scale refrigeration systems, used to help control microbial growth in various processing applications, have helped the food processing industry to remain in compliance with food safety goals. Refrigeration applications and processes are implemented at various locations in the processing operation to ensure maximization of microbiology control and shelf life. Depending on the particular food product being processed—beef, pork, poultry, fish, eggs, nuts, fruits, vegetables, for example—and the particular operation taking place, various methods of achieving this reduction in product temperature are employed. In poultry processing for example, submersion in large chilled water baths is the allowed and preferred method for the rapid reduction in carcass temperature after evisceration.

Immersion chilling has a benefit of an increased "washing effect" which lowers the total microbial load on poultry; however, it is also a potential place for cross contamination to occur. In order to control microbiology in chiller tanks, it is a typical practice to add specialized chemistry to the tanks throughout the processing day. This specialized chemistry, known in the industry as intervention solutions kill or provide a log 10 reduction in the amount of any unwanted microorganisms. There are several antimicrobials that are approved and effective for use in the chiller to decrease pathogens, including, for instance, chlorine, peroxyacetic acid ("PAA"), CPC, organic acids, TSP, acidified sodium chlorite and chlorine dioxide. Because chiller tanks are often quite voluminous, the amount of antimicrobials needed can be quite high to provide a desired log 10 reduction in the amount of any unwanted microorganisms.

PAA, which is also sometimes called peroxyacetic acid, is a peroxycarboxylic acid and is a well known chemical for its strong oxidizing potential, has the molecular formula CH3COOOH, and has a molecular structure as follows:

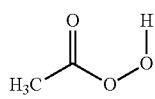

An equilibrium peroxyacetic acid solution is produced from an equilibrium mixture of hydrogen peroxide, acetic acid and water ("equilibrium PAA solution"), which often uses an acid catalyst, e.g., sulfuric acid.

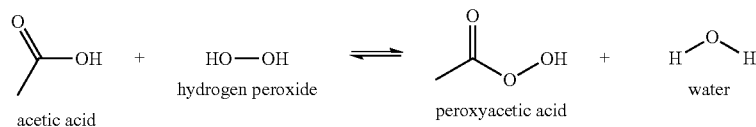

Besides immersion chilling, food products may undergo other processes before being provided to a consumer, such as being dipped, rinsed, washed, sprayed, quenched, soaked, and the like in a chemical intervention solution to reduce or facilitate elimination of the risk of microbial contamination. The use of such chemical intervention solutions in such various food processing processes has recently brought to question the health risks, and possibly the comfort levels, of humans resulting from airborne exposure to such intervention solutions during food processing. Such solutions often include PAA, which has a distinct, pungent odor.

Ideally, vapors of chemical intervention solutions, such as PAA, used in such food processing process are minimized to levels that are healthy and comfortable for workers in the industry. In an effort to regulate comfortable working conditions involving chemical intervention solution, regulatory agencies and associations such as the EPA, ACGIH, and NIOSH, as well as other bodies, have established regulatory guidelines and limits for PAA and associated chemical intervention vapors. In 2014, the ACGIH released a 15 minute short term exposure limit (STEL) for airborne exposure of PAA of 0.4 ppm. NIOSH has proposed an immediately dangerous to life and health (IDLH) level of PAA of 0.55 ppm. These regulatory agencies also have exposure limits of hydrogen peroxide and acetic acid, which are also present in peroxyacetic acid solutions.

Currently, the most widespread way to remove chemicals in the air is through the use of activated carbon. Activated carbon works like a sponge and is capable of adsorbing thousands of different chemicals from the air and is highly effective in both industrial and residential applications. However, because of their size, chemicals such as PAA and other peroxycarboxylic acids, cannot be readily absorbed by activated carbon.

Alternative sources of air purification include respirator cartridges. Respirator cartridges include the 3M organic vapor/acid gas (OV/AG) cartridge, the 3M organic vapor (OV) cartridge, and the 3M multipurpose type (ABEK2P3) cartridge all from 3M manufacturing company headquartered in Maplewood, Minn.; Draeger multipurpose type (A2B2E2K1P2) headquartered in Lubeck, Germany; and Mine Safety Appliance (MSA) multipurpose type (GME) (NIOSH approved for 10 gases and vapors) cartridge from Mine Safety Appliances headquartered in Cranberry Township, Pa. While cartridges can be effective for removing PAA and associated chemicals from the air, they require frequent changing and their effectiveness can be reduced in larger rooms. Therefore, cartridges are often a high maintenance and costly option for air purification. Also, face masks with cartridges are uncomfortable to wear for long periods of time and work less well in very wet environments like food processing plants.

Despite there being various regulatory mandates and guidelines for exposure levels of PAA and various other chemical intervention solution components, there is a need for an efficient and cost-effective resolution to address airborne intervention chemistries that result from food processing, such as a way to efficiently and cost-effectively remove such vapors from the air.

SUMMARY OF THE INVENTION

The present invention is directed at a scrubber system, scrubber assembly and methods of treating malodorous air having chemical vapors at a point of use.

In some aspects, the present invention is directed at a scrubber system that can provide continual treatment of malodorous air containing vapors or a gaseous form of one or more chemical intervention solutions released into the air during food processing. In some aspects, the scrubber system can continually treat a source of air, while in some other aspects, the scrubber system can be used to treat air in a non-continual manner.

In some aspects, the scrubber system of the present invention utilizes a plenum or other air collection means to collect the air to be treated that is in fluid connection with a scrubber assembly that can treat an influent airflow introduced into the scrubber assembly, and the treated airflow transferred to a blower assembly in fluid connection with the scrubber assembly to discharge the treated airflow. In some aspects, the treated airflow is discharged proximate the point of use from which the air was originally collected.

In some aspects, the scrubber assembly comprises a housing with two opposing side walls, opposing front and back walls, and opposing top and bottom walls defining an interior tank volume. In some aspects, the scrubber assembly can have a demisting assembly located between the top and bottom walls, which can define a top interior tank and bottom interior tank, the top interior tank located between the top portion of the scrubber assembly and the top wall, and the bottom interior tank located between the bottom portion of the scrubber assembly and the bottom wall. In some aspects, the bottom interior tank is configured to have a solution tank portion, which is capable of containing a solution, and a headspace tank portion. In some aspects, the headspace tank portion is located above the solution tank portion.

In some aspects, an influent airflow is treated in the scrubber assembly using a neutralizing chemical process using a neutralizing chemical solution in the solution tank portion. In some aspects, the malodorous air streamed into the scrubber assembly is treated by sparging the influent airflow through the neutralizing chemical solution to allow one or more chemical components that are the source of malodorous air to interact with the neutralizing chemical solution and remove at least a portion of the one or more chemical components from the influent airflow to provide a treated effluent airflow that then emanates from the neutralizing chemical solution into the headspace tank portion.

In some aspects, the treated effluent airflow may contain vapors, droplets or the gaseous form of the neutralizing chemical solution and/or reactants formed between the neutralizing chemical solution and components removed from the influent airflow, which can be maintained within the scrubber assembly by a demisting assembly. In some aspects, the treated effluent airflow emanating from the neutralizing chemical solution having any gaseous or resulting vapors or droplets can be streamed from the headspace tank portion through the demisting assembly, whereby the demisting assembly is configured to remove at least a portion of such gaseous, vapor or droplet components, as well as any residual malodorous sources, to further treat the effluent airflow before it is transferred to the blower assembly.

In some aspects, the scrubber assembly can comprise an inlet pipe assembly operably engaged to the front wall. In some aspects, the inlet pipe assembly can be operably configured to receive the influent airflow of malodorous air from outside the housing and discharge the influent airflow into the neutralizing chemical solution contained within the solution tank portion. In some aspects, the scrubber assembly can further comprise an outlet pipe assembly operably engaged to the back wall. In some aspects, the outlet pipe assembly can be operably configured to receive the treated effluent airflow from the top interior tank and transfer the effluent airflow from the housing to the blower assembly. In some aspects, the blower assembly can be configured to discharge the effluent airflow proximate the point of use.

In some aspects, the blower assembly drives the airflow in a continuous manner by providing a draw of influent airflow having the malodorous air at the plenum that is then transferred through the scrubber assembly to provide a treated effluent airflow that is discharged. In some aspects, the blower assembly drives the airflow collection at a point of use in a continuous manner by providing a draw of influent airflow that is introduced into the scrubber assembly to provide a treated effluent airflow that is discharged back proximate the point of use.

In some aspects, use of the scrubber system, scrubber assembly, and method for controlling chemical vapors in air at a point of use comprises transferring an influent airflow containing one or more chemical components to be removed from air at the point of use to the solution tank portion of the scrubber assembly to treat the malodorous air components within the influent airflow with a neutralizing chemical solution to provide a treated effluent airflow, and discharging the effluent airflow proximate the point of use.

In some aspects, the source of malodorous air is one or more gaseous peroxycarboxylic acids that have become airborner. In some aspects, the source of malodorous air is one or more gaseous peroxycarboxylic acid, hydrogen peroxide, carboxylic acid, or a mixture thereof, which have become airborne from chemical intervention solutions used during one or more food processing processes.

In some aspects the gaseous peroxycarboxylic acid causing the malodorous air can include peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof.

In some aspects the gaseous carboxylic acid that is causing the malodorous air is the corresponding carboxylic acid is formic acid, propionic acid, acetic acid, butanoic acid, pentanoic acid, hexanoic acid, heptanoic acid, octanoic acid, nonanoic acid, decanoic acid, undecanoic acid, dodecanoic acid, lactic acid, maleic acid, ascorbic acid, hydroxyacetic acid, oxalic acid, malonic acid, succinic acid, glutaric acid, adipic acid, pimelic acid, subric acid, and mixtures thereof.

In some aspects, the malodorous air for treatment contains peroxyacetic acid, hydrogen peroxide, acetic acid, or mixtures thereof, in a gaseous or vapor form within the air. In some aspects, the airborne peroxyacetic acid, hydrogen peroxide, acetic acid, or mixtures thereof, is the result of one or more food processing processes using a peroxyacetic acid intervention chemistry solution.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
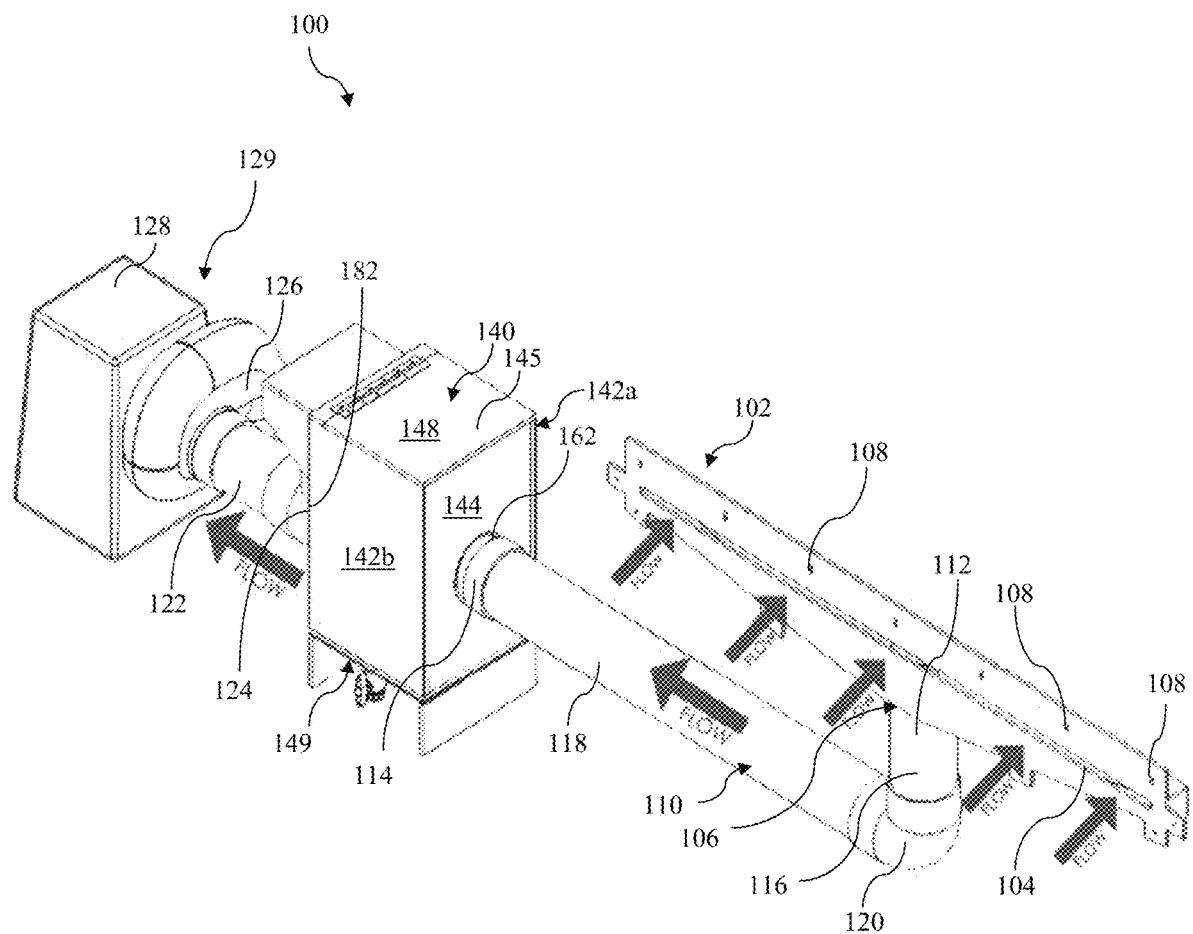
FIG. 1 is perspective view of a scrubber system according to certain embodiments of the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

During food processing, chemical intervention solutions used during the processes can become airborne. In some situations, the quantity of airborne intervention chemistries in the air can be potential concerns for human safety if unsafe levels are reached, or cause comfort, relating to the malodorous air. Since peroxycarboxylic acids, particularly peroxyacetic acid, is one such chemical intervention solution used during food processing, the peroxycarboxylic acid, corresponding carboxylic acid, hydrogen peroxide, or mixtures thereof, can become airborne during food processing contributing to malodorous air. As such, it is desirous to remove such airborne intervention chemistries resulting from food processing from a point of use. The present invention relates to a scrubber system, a scrubber assembly and methods of using a scrubbing assembly for air purification and/or deodorization of malodorous air at a point of use by chemical scrubbing the intervention chemistries causing the malodorous air to provide a treated air that can be returned back to the point of use.

As illustrated in FIG. 1, a scrubber system 100 for controlling chemical vapors in air at a point of use according to an embodiment of the present invention can comprise a plenum 102 in fluid connection with a scrubber assembly 140 that is in fluid connection with a blower assembly 129. As illustrated in FIG. 1, the plenum 102 can include at least one inlet 104 and at least one outlet 106. In some aspects, plenum 102 may have an elongated rectangular shape. In some other aspects the plenum 102 has a shape that is square, round, or any other shape that can gather air from a point of use. Accordingly, it is contemplated that plenum 102 may be configured to any shape to provide adequate collection of air for any particular point of use.

In some aspects, inlet 104 may be a continuous elongate slit. In some other aspects, inlet 104 may be comprised of a plurality of slits or apertures. In some other aspects, inlet 104 may be comprised of a singular slit or aperture. It is contemplated that inlet 104 is configured to be capable of collecting air from the surrounding point of use. In some aspects, inlet 104 is configured to be in fluid connection with outlet 106. While FIG. 1 and the present description disclose a plenum 102, any means for air collection can be utilized that adequately gathers air from the surrounding point of use.

In some aspects, plenum 102 may further comprise one or more attachment locations 108. In some aspects, plenum 102 can be mounted to a wall, frame, or other structural component at a point of use area. In use, attachment locations 108 can operably engage the plenum 102 at a location for mounting or attachment at a point of use area.

With reference to FIG. 1, plenum 102 can be fluidly connected to the scrubber assembly 140 and blower assembly 129. In some aspects, plenum 102 can be configured to receive influent airflow from a point of use to be transferred to the scrubber assembly 140. In some aspects plenum 102 is configured to receive an influent airflow from inlet 104 and discharge the influent airflow from outlet 106 to scrubber 140

Referring to FIG. 1, plenum 102 is fluidly connected to scrubber assembly 140 by upstream piping assembly 110 that extends between plenum 102 and scrubber assembly 140. Upstream piping assembly 110 can include inlet 112 and outlet 114. According to an embodiment, inlet 112 can be configured to receive influent airflow from outlet 106 of plenum 102, and outlet 114 can be configured to discharge influent airflow to scrubber assembly 140, such as by being operably connected with influent receiving end 162. In some aspects, upstream piping assembly 110 can further include an influent air receiving end 116. In some aspects, influent air receiving end 116 is located proximate inlet 112. In some aspects, upstream piping assembly 110 can further include an influent air discharging end 118. In some aspects, influent air discharging end 118 is located proximate outlet 114. According to an embodiment, influent airflow receiving end 116 is in fluid connection with influent airflow discharging end 118.

According to an embodiment, influent airflow receiving end 116 of the upstream piping assembly 110 is substantially perpendicular and extends away from the plenum outlet 106. According to an embodiment, upstream piping 110 comprises an elbow bend 120 located between the influent receiving end 116 and the influent discharging end 118. In some aspects elbow bend 120 is between about 30° and about 150°, in some aspects elbow between about 45° and about 135°, in some aspects between about 60° and about 120°, in some aspects between about 75° and about 105°, and in some preferred aspects about 90°. In some alternative aspects, there is no elbow bend 120 between influent receiving end 116 and the influent discharging end 118.

According to an embodiment, upstream piping assembly 110 extends between plenum 102 and scrubber assembly 140. According to an embodiment, upstream piping assembly 110 is configured to transfer the influent airflow from plenum 102 to scrubber assembly 140 through a length of upstream piping 110.

Referring still to FIG. 1, scrubber assembly 140 is fluidly connected to blower assembly 129 by downstream piping assembly 122 that extends between scrubber assembly 140 and blower assembly 129. In some aspects, downstream piping assembly 122 can include inlet 124 that receives effluent airflow from scrubber assembly 140, such as by being operably connected with effluent discharging end 182, and outlet 126 can be configured to discharge effluent airflow to blower assembly 129. In some aspects, downstream piping assembly 122 operably connects and is in fluid connection with scrubber assembly 140 and blower assembly 129. More specifically, downstream piping assembly inlet 124 operably connects and is in fluid connection with scrubber assembly 140 and downstream piping assembly outlet 126 operably connects and is in fluid connection with blower assembly 129.

According to an embodiment, downstream piping assembly 122 is configured to transfer the effluent airflow from scrubber assembly 140 to blower assembly 129 through a length of the downstream piping assembly 122. In some aspects, downstream piping inlet 124 is configured to receive effluent airflow from the scrubber assembly 140. In some aspects, downstream piping outlet 126 is configured to discharge effluent airflow from scrubber assembly 140 to blower assembly 129. More specifically, downstream piping outlet 126 is configured to discharge the effluent airflow to blower assembly 129.

Referring still to FIG. 1, blower assembly 129 can include a power assembly 128. In some aspects, power assembly 128 provides power to blower assembly 129. In some aspects, power assembly 128 provides power to scrubber system 100.

In some aspects, blower assembly 129 is configured to provide a contiguous draw of influent airflow from a point of use into plenum 102 that is transferred to scrubber assembly 140 where the influent airflow is treated to provide an effluent airflow, which is then transferred from the scrubber assembly 140 to the blower assembly 129 and discharged back to the point of use.

Figure 2A:
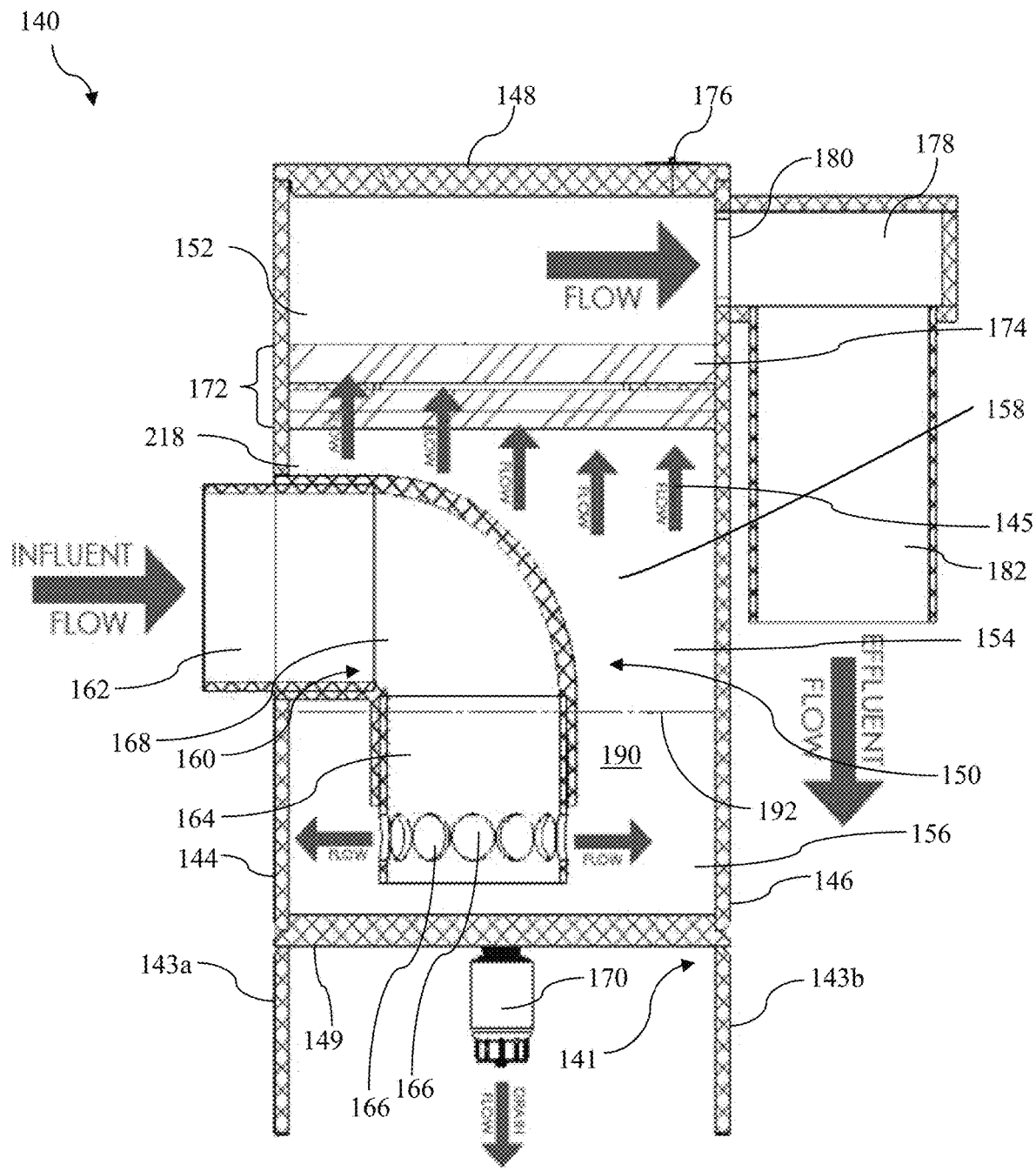
FIG. 2A is a section view of the scrubber assembly of FIG. 1 according to certain embodiments of the present invention.
Figure 2B:
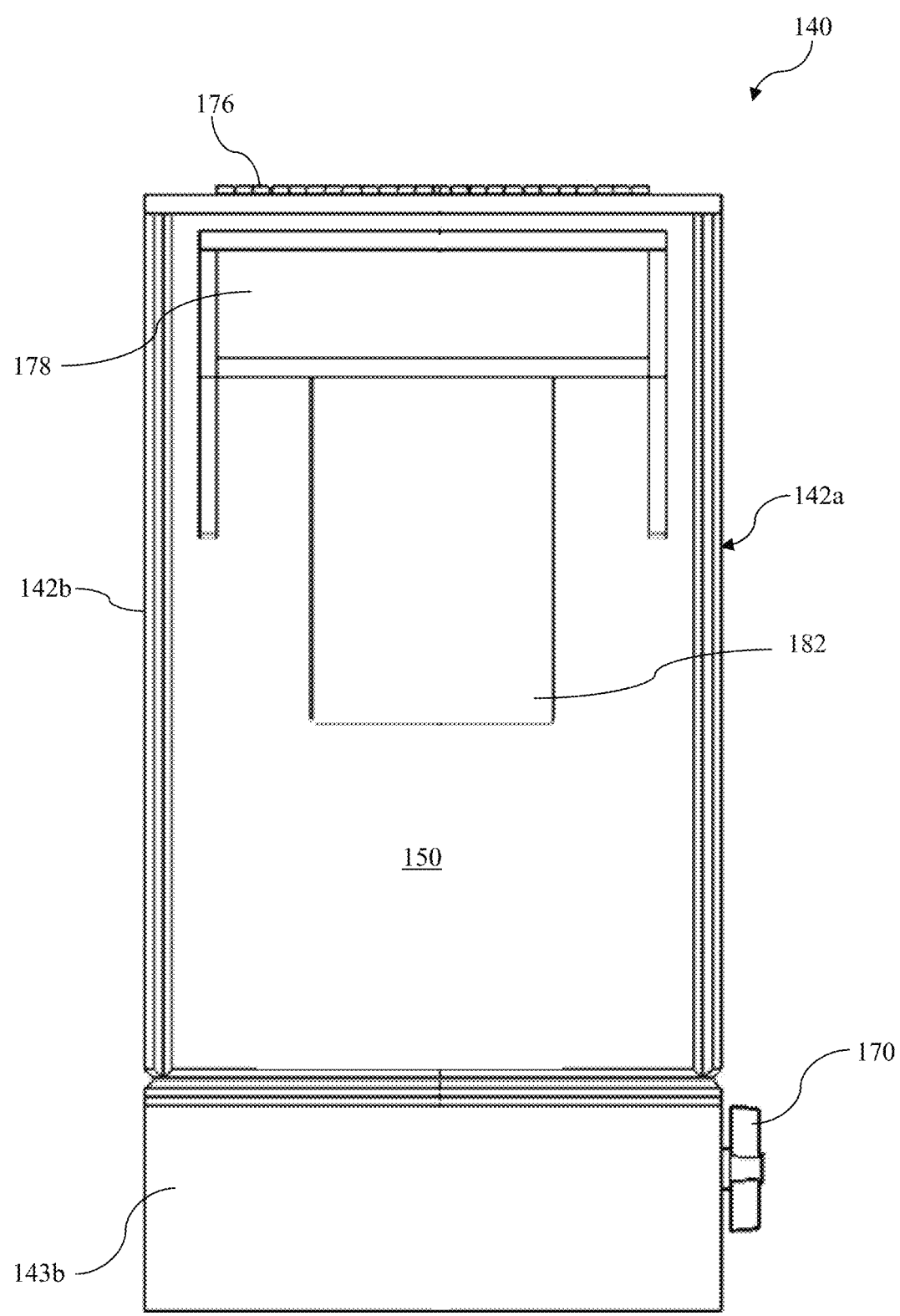
FIG. 2B is a back view of the scrubber assembly of FIG. 2A.

Referring now to FIGS. 1, 2A and 2B, scrubber assembly 140 has a housing 145 having two opposing side walls 142a, 142b front wall 1404 having opposing back wall 146, and top wall 148 having opposing bottom wall 149, defining an interior tank volume 150.

According to certain aspects, scrubber assembly 140 can be comprised of a metal material. In some aspects the metal material can be steel, stainless steel, aluminum, or a metal alloy. In an alternative aspect, scrubber assembly 140 can be comprised of a plastic material.

According to an embodiment, top wall 148 can be integral with housing 145. In some aspects, top wall 148 can be configured to operably engage with at least one of the opposing side walls 142a, 142b, front wall 144, back wall 146, or combinations thereof. In some aspects, top wall 148 can operably engage with an engagement portion located on least one of the opposing side walls 142a, 142b, front wall 144, back wall 146, or combinations thereof. In some aspects, engagement portion can be peripheral ledge running around the interior of housing 145. In some aspects, the engagement portion can be comprised of one or more tabs located on the one or more opposing side walls 142a, 142b, front wall 144, or back wall 146.

According to an embodiment, top wall 148 is capable of being opened or openable. As illustrated in FIGS. 2A and 2B, top wall 148 can include a hinge 176. In some aspects, hinge 176 allows top wall 148 unrestricted movement in a direction upward and away from the housing 145.

According to an embodiment, one or more opposing side walls, 142a, 142b, front wall 144, back wall 146, top wall 148, and/or bottom wall 149, can comprise a window. In some aspects, the window allows for observation into one or more portions of the interior tank volume 150. In some aspects, one or more opposing side walls, 142a, 142b, front wall 144, back wall 146, top wall 148, and/or bottom wall 149, can comprise a closeable opening. In some aspects, the closeable opening allows for observation of the interior tank volume 150. In some alternative aspects, as least a portion of one or both opposing side walls 142a, 142b, front wall 144, back wall 146, top wall 148, bottom wall 149, or a combination thereof, can comprise a transparent material allowing observation into interior tank volume 150. In some other aspects, at least a lower portion of at least one side wall 142a, 142b, front wall 144 and/or back wall 146, can comprise a transparent material allowing observation into interior tank volume 150.

In some aspects, scrubber assembly 140 further comprises a scrubber support frame 141 to elevate bottom wall 149 off the ground. In some aspects, scrubber support frame 141 includes at least two legs 143a, 143b. In some aspects, legs 143a, 143b extend away from the bottom wall 149. In some aspects, legs 143a, 143b are perpendicular to bottom wall 149. In some aspects, legs 143a, 143b, have a length and width that is substantially the same as the opposing front and back walls 144,146. According to an alternative embodiment, scrubber assembly 140 can further include a support frame 141 that includes four legs extending away from a corner of the housing 145 proximate the bottom wall 149. In some aspects, each of the four legs may extend perpendicular to bottom wall 149.

According to an embodiment as illustrated in FIGS. 2A and 2B, scrubber assembly 140 may include a valve 170. In some aspects, valve 170 provides a drain for housing 145. In some other aspects, valve 170 is a controllable release assembly. In some aspects, valve 170 can be located on an opposing side wall 142a or 142b. In some aspects, valve 170 can be located on front wall 144 or alternatively on back wall 146. In some preferred aspects, valve 170 is located on bottom wall 149. In some aspects, valve 170 is located between legs 143a, 143b of scrubber support frame 141 proximate bottom wall 149. In some aspects, valve 170 extends away from bottom wall 149 in a perpendicular configuration.

Valve 170 can be configured to allow for introduction of a solution into housing 145 of scrubber assembly 140. In some aspects, valve 170 can be configured to allow for discharge of liquid contents, such as a solution, from housing 145 of scrubber assembly 140. In some aspects, as discussed further below, valve 170 can be used to discharge a spent neutralizing solution and any reactant products contained within solution tank portion 156 of housing 145.

Referring still now to FIGS. 2A and 2B, scrubber assembly 140 can include a demisting assembly 172. As illustrated in FIG. 2A, demisting assembly 172 can be located between the top wall 148 and the bottom wall 149. In some aspects, demisting assembly 172 is operably engaged to at least one of the opposing side walls 142a, 142b, front wall 144, back wall 146, or combinations thereof. In some aspects, demisting assembly 172 is substantially perpendicular to opposing side walls 142a, 142b, front wall 144, and back wall 146. In some aspects, demisting assembly 172 is configured to have a dimension that fits within the space provided by opposing side walls 142a, 142b and opposing front and back walls 144, 146.

In some aspects, demisting assembly 172 can be integral with scrubber housing 145. In some aspects, demisting assembly 172 can be integral with one or more opposing side walls 142a, 142b, front wall 144, or back wall 146

In some aspects, demisting assembly 172 is operably engageable with at least one of the opposing side walls 142a, 142b, front wall 144, or back wall 146, such that the demisting assembly 172 is operably removable from housing 145. In an alternative aspect, demisting assembly 172 can operably engage with an engagement portion located on at least one of the opposing side walls 142a, 142b, front wall 144, and back wall 146. In some aspects, engagement portion can be peripheral ledge running around the interior of housing 145 on one or more of opposing side walls 142a, 142b, front wall 144, and back wall 146. In some aspects, the engagement portion can be comprised of one or more tabs located on the one or more opposing side walls 142a, 142b, front wall 144, and back wall 146.

In some aspects, demisting assembly 172 contained within housing 145 can define a top interior tank 152 located between demisting assembly 172 and top wall 148.

In some aspects, demisting assembly 172 contained within housing 145 can define a bottom interior tank 154 located between demisting assembly 172 and bottom wall 149. In some aspects, bottom interior tank 154 is configured to have a solution tank portion 156 and a headspace tank portion 158, with the headspace tank portion 158 located above the solution tank portion 156.

In some aspects, demisting assembly 172 can comprise at least one demisting gradient 174. In some alternative aspect, demisting assembly 172 comprises a plurality of demisting gradients 174. In some aspects, a plurality of demisting gradients 174 can be arranged in a successive manner, such that the demisting gradients 174 have a stacked configuration. In some aspects, there is a space between at least two successively arranged demisting gradients 174. In some other aspects, at least two successively arranged demisting gradients 174 are adjacent to and in contact with each other. In some aspects, demisting gradient 174 is one or more screens, filters, baffles, or combinations thereof. In some aspects, the one or more demisting gradient 174 may comprise one or more S-shaped or V-shaped baffles.

According to an embodiment, solution tank portion 156 can be configured to house a liquid component, preferably a solution 190. In some aspects, solution 190 is a neutralizing solution, more preferably a chemical neutralizing solution

190. In some aspects, the chemical neutralizing solution 190 is configured to treat one or more chemical components in the influent airflow.

In some aspects, the influent airflow contains one or more chemical components in a gaseous or vapor form, and chemical neutralizing solution 190 is capable of reacting, absorbing, adsorbing, or otherwise interacting with the one or more chemical components to remove the one or more components from the influent airflow sparged through the chemical neutralizing solution and retain the one or more chemical components in the chemical neutralizing solution 190. According to certain embodiments, representative gaseous or chemical vapors that can be removed from the influent airflow by the chemical neutralizing solution 190 include one or more peroxycarboxylic acids, carboxylic acids, hydrogen peroxide, or combinations thereof.

In some aspects a peroxycarboxylic acid can include peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof.

In some aspects, the carboxylic acid can include formic acid, propionic acid, acetic acid, butanoic acid, pentanoic acid, hexanoic acid, heptanoic acid, octanoic acid, nonanoic acid, decanoic acid, undecanoic acid, dodecanoic acid, lactic acid, maleic acid, ascorbic acid, hydroxyacetic acid, oxalic acid, malonic acid, succinic acid, glutaric acid, adipic acid, pimelic acid, subric acid, and mixtures thereof.

In some aspects, the influent airflow contains peroxyacetic acid, acetic acid, hydrogen peroxide, or combinations thereof, in a gaseous or vapor form, and chemical neutralizing solution 190 is capable of reacting, absorbing, adsorbing, or otherwise interacting with one or more of these chemical components to remove the chemical components from the influent airflow by sparging the influent airflow through the chemical neutralizing solution, which retains the one or more chemical components in the chemical neutralizing solution 190.

In some aspects, neutralizing chemistry solution 190 can be premixed and introduced into solution tank portion 156 as a liquid. In some other aspects, neutralizing chemistry solution 190 can be prepared in solution tank portion 156 by mixing a solution with one or more neutralizing chemistry components. In some aspects, neutralizing chemistry components can be introduced as a liquid, while in other aspects in the form of a powder, tablet or other solid. In some preferred aspects, neutralizing chemical solution 190 comprises a water-based solution having one or more neutralizing chemistry components. In some aspects, neutralizing solution 190 comprises one or more neutralizing chemistry components that are capable of interacting with one or more chemical components that are desirable to be removed from the influent airflow. In some aspects, neutralizing solution 190 comprises one or more neutralizing chemistry components that are capable of interacting with one or more airborne peroxycarboxylic acids that are desirable to be removed from the influent airflow. In some aspects, neutralizing solution 190 comprises one or more neutralizing chemistry components that are capable of interacting with at least one airborne peroxycarboxylic acid, corresponding carboxylic acid, hydrogen peroxide, or mixtures thereof, that are desirable to be removed from the influent airflow. In some aspects, neutralizing solution 190 comprises one or more neutralizing chemistry components that are capable of interacting with airborne peroxyacetic acid to be removed from the influent airflow. In some aspects, neutralizing solution 190 comprises one or more neutralizing chemistry components that are capable of interacting with airborne peroxyacetic acid, hydrogen peroxide, acetic acid, or mixtures thereof, to be removed from the influent airflow. One of ordinary skill in the art will appreciate that there can be a wide array of neutralizing chemistry components that are satisfactory for removing the desirable chemical components from the influent airflow. Without wishing to be bound by theory, the neutralizing chemistry components may remove the one or more chemical components from the influent air by one or more interactions of covalent bonding, ionic bonding, absorbing, adsorbing, complexing, Vander wall forces, reacting, and the like. Exemplary neutralizing chemistry components for removal of airborne peroxycarboxylic acid solutions used during food processing, particularly peroxyacetic acid solutions, include sodium metabisulfate, sodium bisulfate, sodium bicarbonate, sodium carbonate, sodium thiosulfate, sodium thiosulfate pentahydrate, anhydrous sodium thiosulfate, and combinations thereof.

In some aspects, the neutralizing chemistry solution 190 can include an indicator added to the neutralizing chemistry solution 190, wherein the indicator is configured to indicate when the neutralizing chemistry solution can no longer remove the one or more desired components from the influent airflow, such as indicating when the neutralizing chemistry solution has become spent or exhausted. In some aspects, the indicator can be a peroxide group indicator, redox indicator, or pH indicator. Exemplary indicators include potassium iodide, sodium iodide, and combinations thereof.

After removal of one or more desired chemical components from the influent airflow, the effluent airflow emanating from the neutralizing chemistry solution 190 may contain small droplets or the vapor form of the neutralizing chemistry solution 190, water, reactant solution, or combinations thereof. One of ordinary skill in the art will appreciate that the term "reactant solution" will refer to the interacted form between the one or more chemical components removed from the influent airflow and the neutralizing chemistry components, whether by covalent bonding, ionic bonding, absorbing, adsorbing, complexing, Vander wall forces, reacting, and the like. In some aspects, demisting assembly 172 can be configured to remove from the effluent airflow at least a portion of the neutralizing chemistry solution 190, water, reactant solution, or combinations thereof, as the effluent airflow transfers between the headspace tank portion 158 and the top interior tank 152. In some aspects, the droplets collide with demisting assembly 172 and are captured from the effluent airflow by becoming adhered to the demisting assembly 172 where adhered droplets coalesce and fall away or drip from the demisting assembly 172 back into the neutralizing chemistry solution 190 held within solution tank portion 156. In some aspects, the demisting assembly 172 maintains the proper level of neutralizing chemistry solution 190 within solution tank portion 156 by removal of water droplets in the effluent airflow.

Referring still to FIG. 2A, scrubber assembly 140 can include an inlet pipe assembly 160. In some aspects, inlet pipe assembly 160 can include an influent receiving end 162 in fluid connection with influent discharging end 164. In some aspects influent receiving end 162 is operably engaged to the front wall 144. In some aspects, influent receiving end 162 is operably configured to receive influent airflow from outside housing 145. As illustrated in FIG. 2A, influent receiving end 162 can be perpendicular to and extending away from an internal face of front wall 144.

In some aspects, influent discharging end 164 can be configured to discharge the influent airflow into the solution tank portion 156. As illustrated in FIG. 2A, influent discharging end 164 can be perpendicular to influent receiving end 162. In some aspects, influent discharging end 164 can be extending away from influent receiving end 162 with influent discharging end 164 located within a neutralizing chemistry solution 190 and influent receiving end 162 located out of neutralizing chemistry solution 190.

In some aspects, influent discharging end 164 is located within solution tank portion 156 while at least a portion of influent receiving end 162 is located within headspace tank portion 158. In some aspects, influent discharging end 164 can comprise a plurality of air inlet apertures 166. In some aspects, air inlet apertures 166 can be located proximate the periphery of the distal end of the influent discharging end 164. According to an embodiment, during normal operation, influent discharging end 164 can be submerged in neutralizing chemistry solution 190, such that influent airflow is sparged through neutralizing chemistry solution 190 before emanating into headspace tank portion 158. In some preferable aspects, the air inlet apertures 166 are located below a neutralizing chemistry solution level 192 within the solution tank portion 156.

In some aspects, inlet pipe assembly 160 can comprise an elbow bend 168 located between influent receiving end 162 and influent discharging end 164. In some aspects, elbow bend 168 is between about 30° and about 150°, in some aspects between about 45° and about 135°, in some aspects between about 60° and about 120°, in some aspects between about 75° and about 105°, and in some preferred aspects about 90°.

In some aspects, influent receiving end 162 can be configured to receive a horizontal airflow of influent air and direct the influent air to elbow bend 168. In some aspects, elbow bend 168 is configured to receive substantially horizontal influent airflow air and direct the influent air to a substantially vertical influent airflow to discharging end 164 and out of the plurality of air inlet apertures 166 into neutralizing chemistry solution 190.

In some aspects, influent airflow is capable of being sparged through neutralizing chemistry solution 190 contained in solution tank portion 156 of the scrubber assembly 140. In some aspects, the headspace tank portion is configured to receive the effluent airflow as the influent airflow treated within the neutralizing chemistry solution 190 and then transferred from the solution tank portion 156 to the headspace tank portion 158. In some aspects, the top interior tank 152 is configured to receive the effluent airflow as the effluent airflow is transferred from the headspace tank portion 158 through the demisting assembly 172 to the top interior tank 152.

In some aspects, headspace tank portion 158 allows treated effluent airflow to flow unrestricted to demisting assembly 172. In some aspects, top interior tank 152 allows for effluent airflow from headspace portion 158. In some aspects, top interior tank 152 is configured to further allow unrestricted effluent airflow from the top interior tank 152 to outlet pipe assembly 178. In some aspects, outlet pipe assembly 178 allows effluent airflow from the top interior tank 152 to outside housing 145.

Referring still to FIG. 2A, scrubber assembly 140 can further include an outlet pipe assembly 178. In some aspects, outlet pipe assembly can include an effluent receiving end 180 in fluid connection with an effluent discharging end 182. In some aspects, effluent receiving end 180 can be operably engaged to back wall 146. In some aspects, effluent receiving end 180 can be operably configured to receive effluent airflow from the top interior tank portion 152 and transfer the effluent airflow to outside scrubber assembly 140. In some aspects, effluent receiving end 180 is perpendicular to and extending away from an external face of the back wall 146. In some aspects, the effluent discharging end 182 is perpendicular to and extending away from the effluent receiving end 180. In some aspects, effluent discharging end 182 operably engages with effluent receiving end 180 at a bottom or ventral portion of effluent receiving end 180. In some aspects, air received from effluent receiving end 180 is directed down toward effluent discharging end 182 and out of housing 145 to a point of use.

The scrubber system 100 and scrubber assembly 140 shown in FIGS. 1, 2A and 2B, can be used in a method to remove airborne vapors from a chemical intervention process chosen from a dip tank process, cabinet wash, scalding assembly, spraying assembly, or combinations thereof.

In some aspects, a method of treating air at a point of use in a food processing operation can comprise collecting an influent airflow from a point of use in the food processing operation using a plenum 102 in fluid connection with a scrubber assembly 140 and a blower assembly 128. The influent airflow can be sparged through a neutralizing chemistry solution 190 contained within scrubber assembly 140 to remove one or more chemical components and provide a treated effluent airflow. The effluent airflow can be streamed through a demisting assembly 174 to remove any particles of droplets of neutralizing chemistry solution 190, reactant products, or water, to provide a treated effluent airflow, before the treated effluent airflow being transferred to the blower assembly 128 and discharged back into the point of use.

In some aspects, the method can comprise forming a neutralizing chemistry solution 190 to be contained within the scrubber assembly 140. Neutralizing chemistry solution 190 can be formed from water, a water solution, a powder, a tablet, a liquid solution, or combinations thereof. In some aspects an indicator can be incorporated into solution 190. In some aspects, the indicator can change colors indicate when the solution is spent.

According to some aspects, when neutralizing chemistry solution 190 is determined to be spent, neutralizing chemistry solution 190 can be drained from valve 170 and discarded from scrubber assembly 140. According to an embodiment, when a solution is spent, the solution can be replaced. In some aspects, solution can be replaced through valve 170. In some aspects, solution can be replaced by using hinge 176 and opening top wall 148 to gain access to interior tank volume 150. In an alternative aspect, if solution 190 level is too high, valve 170 can be used to drain a desired amount of the solution.

In some preferred aspects of the present invention, the scrubber system of the present invention is used to remove peroxyacetic acid, acetic acid, hydrogen peroxide, or combinations thereof, in a vaporous form produced from a chemical intervention solution during food processing. In some aspects, an influent airflow is collected from a point of use, the influent airflow having peroxyacetic acid, acetic acid, hydrogen peroxide, or combinations thereof, in a vaporous form. The influent airflow is subjected to a neutralizing chemistry solution 190 contained within scrubber assembly 140. In some aspects, the influent airflow is sparged through neutralizing chemistry solution 190 within scrubber assembly 140 to allow neutralizing chemistry solution 190 to react, absorb, adsorb, or otherwise interact with one or more of these chemical components in influent airflow and provide a treated effluent airflow having reduced levels of peroxyacetic acid, acetic acid, hydrogen peroxide, or combinations thereof. The treated effluent airflow may be subjected to a demisting assembly to remove any droplets of neutralizing chemistry solution 190, reactant products, or water, before exiting the scrubber assembly and discharged back to the point of use by the blower assembly 129.

In some aspects, the influent airflow contains a level of one or more peroxycarboxylic acids that is greater than 0.4 ppm and the treated effluent airflow contains a level of the one or more peroxycarboxylic acids that is less than 0.4 ppm. In some aspects, the treated effluent airflow contains a total level of peroxycarboxylic acids in an amount less than about 0.4 ppm, preferably less than about 0.3 ppm, preferably less than about 0.25 ppm, preferably less than about 0.2 ppm, preferably less than about 0.15 ppm, preferably less than about 0.1 ppm, preferably less than about 0.05 ppm.

In some aspects, the influent airflow contains a level of peroxyacetic acid that is greater than 0 ppm and the treated effluent airflow contains a level of peroxyacetic acid that is lower than the influent airflow. In some aspects, the treated effluent airflow contains peroxyacetic acid in an amount less than about 0.4 ppm, preferably less than about 0.3 ppm, preferably less than about 0.25 ppm, preferably less than about 0.2 ppm, preferably less than about 0.15 ppm, preferably less than about 0.1 ppm, preferably less than about 0.05 ppm. Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

In some aspects, the treated airflow effluent can be tested for the level of peroxycarboxylic acid, such as peroxyacetic acid, using a monitor. The monitor is preferably located proximate the air intake, the air discharge, or a monitor located at each location. In some aspects, the one or more monitors may provide a signal to a control circuit to increase or decrease the flow of air through the system.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A scrubber system comprising:
   a plenum in fluid connection with a scrubber assembly, the scrubber assembly in fluid connection with a blower assembly;
   wherein the plenum is configured to receive an influent airflow from a point of use to be transferred to the scrubber assembly for treatment;
   wherein the scrubber assembly comprises:
      a housing having opposing side walls, opposing front and back walls, and opposing top and bottom walls, defining an interior tank having a volume;
      a demisting assembly located within the housing between the top and bottom walls, wherein the interior tank has a top interior tank and a bottom interior tank separated by the demisting assembly, wherein the top interior tank is located between an upper surface of the demisting assembly and the top wall, and the bottom interior tank is located between a bottom surface of the demisting assembly and the bottom wall, and wherein the bottom interior tank is configured to have a solution tank portion and a headspace tank portion, the headspace tank portion located above the solution tank portion;
      an inlet pipe assembly operably engaged to the front wall and operably configured to receive the influent airflow from outside the housing and discharge the influent airflow at an influent discharging end located proximate to the solution tank portion;
      a solution contained within the solution tank portion that is capable of removing at least one chemical component comprising one or more peroxycarboxylic acids from the influent airflow to provide a treated effluent airflow into the top interior tank; and
      an outlet pipe assembly operably engaged to the back wall and operably configured to receive the effluent airflow from the top interior tank and transfer the effluent airflow from the housing to the blower assembly;
   wherein the blower assembly is configured to discharge the effluent airflow proximate the point of use.

2. The scrubber system of claim 1, wherein the demisting assembly is configured to remove gaseous, vapor or droplet components from the treated effluent airflow as the effluent airflow is transferred from the headspace tank portion of the bottom interior tank to the top interior tank.

3. The scrubber system of claim 1, wherein the influent discharging end is configured to discharge the influent airflow into the solution contained within the solution tank portion.

4. The scrubber system of claim 3, wherein the inlet pipe assembly comprises an influent receiving end to receive the influent airflow from outside the housing that is in fluid connection with the influent discharging end.

5. The scrubber system of claim 4, wherein the influent receiving end is configured in the housing to be located out of the solution and the influent discharging end is configured in the housing to be submerged within the solution contained within the solution tank portion.

6. The scrubber system of claim 5, wherein the influent discharging end comprises a plurality of air inlet apertures to sparge the influent airflow within the solution.

7. The scrubber system of claim 1, wherein the at least one chemical component further comprises hydrogen peroxide, one or more carboxylic acids, or combinations thereof.

8. The scrubber system of claim 1, wherein the one or more peroxycarboxylic acids is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, or combinations thereof.

9. The scrubber system of claim 1, wherein the at least one chemical component further comprises one or more carboxylic acid chosen from formic acid, propionic acid, acetic acid, butanoic acid, pentanoic acid, hexanoic acid, heptanoic acid, octanoic acid, nonanoic acid, decanoic acid, undecanoic acid, dodecanoic acid, lactic acid, maleic acid, ascorbic acid, hydroxyacetic acid, oxalic acid, malonic acid, succinic acid, glutaric acid, adipic acid, pimelic acid, subric acid, and mixtures thereof.

10. The scrubber system of claim 1, wherein the one or more peroxycarboxylic acids comprise peroxyacetic acid, hydrogen peroxide, acetic acid, or combinations thereof.

11. The scrubber system of claim 7, wherein the solution comprises a neutralizing chemistry solution, the neutralizing chemistry comprising sodium metabisulfate, sodium bisulfate, sodium bicarbonate solution, sodium carbonate, sodium thiosulfate, sodium thiosulfate pentahydrate, anhydrous sodium thiosulfate, or combinations thereof.

12. The scrubber system of claim 11, wherein the neutralizing chemistry solution further comprises an indicator configured to indicate when the neutralizing chemistry solution no longer removes the at least one or more chemical component.

13. The scrubber system of claim 1, wherein the demisting assembly is operably engageable with at least one of the opposing side walls, the front wall, the back wall, the top wall, or combinations thereof, such that the demisting assembly is removable from the housing.

14. The scrubber system of claim 1, wherein the demisting assembly is selected from the group consisting of a screen, a filter, a baffle, or combinations thereof.

15. The scrubber system of claim 1, wherein the influent airflow contains a level of one or more peroxycarboxylic acids that is greater than the treated effluent airflow.

16. The scrubber system of claim 15, wherein the influent airflow contains a level of one or more peroxycarboxylic acids that is greater than 0.4 ppm and the treated effluent airflow contains a level of the one or more peroxycarboxylic acids that is less than 0.25 ppm.

17. The scrubber system of claim 16, wherein the influent airflow contains a level of one or more peroxycarboxylic acids that is greater than 0.4 ppm and the treated effluent airflow contains a level of the one or more peroxycarboxylic acids that is less than 0.1 ppm.

18. A scrubber assembly comprising:
a housing having opposing side walls, opposing front and back walls, and opposing top and bottom walls, defining an interior tank having a volume;
a demisting assembly located within the housing between the top and bottom walls, wherein the interior tank has a top interior tank and a bottom interior tank separated by the demisting assembly, wherein the defining a top interior tank is located between an upper surface of the demisting assembly and the top wall, and the bottom interior tank is located between a bottom surface of the demisting assembly and the bottom wall, and wherein the bottom interior tank is configured to have a solution tank portion and a headspace tank portion, the headspace tank portion located above the solution tank portion;
an inlet pipe assembly operably engaged to the front wall and operably configured to receive an influent airflow from outside the housing and discharge the influent airflow at an influent discharging end located proximate to the solution tank portion; and
an outlet pipe assembly operably engaged to the back wall and operably configured to receive a treated effluent airflow from the top interior tank and transfer the effluent airflow from the housing to a blower assembly;
wherein the influent airflow contains a level of one or more peroxycarboxylic acids that is greater than the treated effluent airflow.

19. A method of controlling chemical vapors in the air at a point of use in a food processing operation, the method comprising:
collecting an influent airflow from the point of use in the food processing operation using a plenum in fluid connection with a scrubber assembly and a blower assembly, wherein the influent airflow contains a level of one or more peroxycarboxylic acids that is greater than 0.4 ppm, wherein the scrubber assembly comprising a housing having opposing side walls, opposing front and back walls, and opposing top and bottom walls, defining an interior tank having a volume,
wherein a demisting assembly located between the top and bottom walls defines a top interior tank located between an upper surface of the demisting assembly and the top wall and a bottom interior tank located between a bottom surface of the demisting assembly and the bottom wall, the bottom interior tank being configured to have a solution tank portion and a headspace tank portion, the headspace tank portion located above the solution tank portion, wherein the plenum is located outside the housing of the scrubber assembly, and wherein an inlet pipe assembly is operably engaged to the front wall and is operably configured to receive the influent airflow from the plenum located outside the housing and discharge the influent airflow into a solution contained within the solution tank portion, and wherein an outlet pipe assembly is operably engaged to the back wall and is operably configured to receive a treated effluent airflow from the top interior tank and transfer the treated effluent airflow from the housing to the blower assembly;

transferring the influent airflow from the plenum into the solution contained within the solution tank portion of the scrubber assembly;

reacting one or more chemical vapors contained in the influent airflow with the solution to produce an effluent airflow having the one or more chemical vapors removed;

flowing the effluent airflow through the demisting assembly to remove at least a portion of any residual vapor solution from the effluent airflow to provide the treated effluent airflow having a level of the one or more peroxycarboxylic acids that is less than 0.1 ppm;

transferring the treated effluent airflow from the scrubber assembly to the blower assembly; and discharging the treated effluent airflow from the blower assembly back to the point of use.

20. A scrubber system comprising:

a plenum in fluid connection with a scrubber assembly, the scrubber assembly in fluid connection with a blower assembly;

wherein the plenum is configured to receive an influent airflow from a point of use to be transferred to the scrubber assembly for treatment;

wherein the scrubber assembly comprises:

a housing having opposing side walls, opposing front and back walls, and opposing top and bottom walls, defining an interior tank having a volume;

a demisting assembly located within the housing between the top and bottom walls, wherein the interior tank has a top interior tank and a bottom interior tank separated by the demisting assembly, wherein the top interior tank is located between an upper surface of the demisting assembly and the top wall, and the bottom interior tank is located between a bottom surface of the demisting assembly and the bottom wall, and wherein the bottom interior tank headspace tank portion located above the solution tank portion;

an inlet pipe assembly operably engaged to the front wall and operably configured to receive the influent airflow from outside the housing and discharge the influent airflow at an influent discharging end located proximate to the solution tank portion;

a solution contained within the solution tank portion that is capable of removing one or more peroxycarboxylic acids, one or more carboxylic acids, or combinations thereof from the influent airflow to provide a treated effluent airflow into the top interior tank; and an outlet pipe assembly operably engaged to the back wall and operably configured to receive the treated effluent airflow from the top interior tank and transfer the treated effluent airflow from the housing to the blower assembly;

wherein the blower assembly is configured to discharge the treated effluent airflow proximate the point of use.

21. The scrubber system of claim 20, wherein the one or more peroxycarboxylic acids is in gaseous or vapor form.

22. The scrubber system of claim 20, wherein the demisting assembly is configured to remove gaseous, vapor or droplet components from the treated effluent airflow as the effluent airflow is transferred from the headspace tank portion of the bottom interior tank to the top interior tank.

23. The scrubber system of claim 20, wherein the influent discharging end is configured to discharge the influent airflow into the solution contained within the solution tank portion.

24. The scrubber system of claim 23, wherein the inlet pipe assembly comprises an influent receiving end to receive the influent airflow from outside the housing that is in fluid connection with the influent discharging end.

25. The scrubber system of claim 24, wherein the influent receiving end is configured in the housing to be located out of the solution and the influent discharging end is configured in the housing to be submerged within the solution contained within the solution tank portion.

26. The scrubber system of claim 25, wherein the influent discharging end comprises a plurality of air inlet apertures to sparge the influent airflow within the solution.

27. The scrubber system of claim 20, wherein the solution contained within the solution tank portion is capable of further removing hydrogen peroxide.

28. The scrubber system of claim 20, wherein the one or more peroxycarboxylic acids is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, or combinations thereof.

29. The scrubber system of claim 20, wherein the one or more carboxylic acid are chosen from formic acid, propionic acid, acetic acid, butanoic acid, pentanoic acid, hexanoic acid, heptanoic acid, octanoic acid, nonanoic acid, decanoic acid, undecanoic acid, dodecanoic acid, lactic acid, maleic acid, ascorbic acid, hydroxyacetic acid, oxalic acid, malonic acid, succinic acid, glutaric acid, adipic acid, pimelic acid, subric acid, and mixtures thereof.

30. The scrubber system of claim 20, wherein the solution contained within the solution tank portion is capable of removing one or more peroxycarboxylic acids comprising peroxyacetic acid and one or more carboxylic acids comprising acetic acid.

31. The scrubber system of claim 30, wherein the solution contained within the solution tank portion is further capable of removing hydrogen peroxide.

32. The scrubber system of claim 20, wherein the solution comprises a neutralizing chemistry solution, the neutralizing chemistry comprising sodium metabisulfate, sodium bisulfate, sodium bicarbonate solution, sodium carbonate, sodium thiosulfate, sodium thiosulfate pentahydrate, anhydrous sodium thiosulfate, or combinations thereof.

33. The scrubber system of claim 32, wherein the neutralizing chemistry solution further comprises an indicator configured to indicate when the neutralizing chemistry solution no longer removes one or more chemical components.

34. The scrubber system of claim 20, wherein the demisting assembly is operably engageable with at least one of the opposing side walls, the front wall, the back wall, the top wall, or combinations thereof, such that the demisting assembly is removable from the housing.

35. The scrubber system of claim 20, wherein the demisting assembly is selected from the group consisting of a screen, a filter, a baffle, or combinations thereof.

36. The scrubber system of claim 20, wherein the influent airflow contains a level of the one or more peroxycarboxylic acids that is greater than the treated effluent airflow.

37. The scrubber system of claim 15, wherein the influent airflow contains a level of the one or more peroxycarboxylic acids that is greater than 0.4 ppm and the treated effluent airflow contains a level of the one or more peroxycarboxylic acids that is less than 0.25 ppm.

38. The scrubber system of claim 37, wherein the influent airflow contains a level of one or more peroxycarboxylic acids that is greater than 0.4 ppm and the treated effluent airflow contains a level of the one or more peroxycarboxylic acids that is less than 0.1 ppm.

39. A scrubber system comprising:
- a housing having opposing side walls, opposing front and back walls, and opposing top and bottom walls, defining an interior tank having a volume;
- a demisting assembly located within the housing between the top and bottom walls, wherein the interior tank has a top interior tank and a bottom interior tank separated by the demisting assembly, wherein the top interior tank is located between an upper surface of the demisting assembly and the top wall, and the bottom interior tank is located between a bottom surface of the demisting assembly and the bottom wall, and wherein the bottom interior tank is configured to have a solution tank portion and a headspace tank portion, the headspace tank portion located above the solution tank portion;
- an inlet pipe assembly operably engaged to the front wall and operably configured to receive an influent airflow from outside the housing and discharge the influent airflow at an influent discharging end proximately located the solution tank portion; and
- an outlet pipe assembly operably engaged to the back wall and operably configured to receive a treated effluent airflow from the top interior tank and transfer the effluent airflow from the housing to a blower assembly;
- wherein the influent airflow contains a level of one or more peroxycarboxylic acids that is greater than 0.4 ppm and the treated effluent airflow contains a level of the one or more peroxycarboxylic acids that is less than 0.25 ppm.

40. The scrubber system of claim 39, further comprising a neutralizing chemistry solution contained within the solution tank portion for treating the influent airflow, wherein the neutralizing chemistry comprising sodium metabisulfate, sodium bisulfate, sodium bicarbonate solution, sodium carbonate, sodium thiosulfate, sodium thiosulfate pentahydrate, anhydrous sodium thiosulfate, or combinations thereof.

41. The scrubber system of claim 39, wherein one or more peroxycarboxylic acids is peroxyacetic acid.

42. The scrubber system of claim 41, wherein a level of peroxyacetic acid in the treated effluent airflow is less than 0.1 ppm.

* * * * *